United States Patent [19]

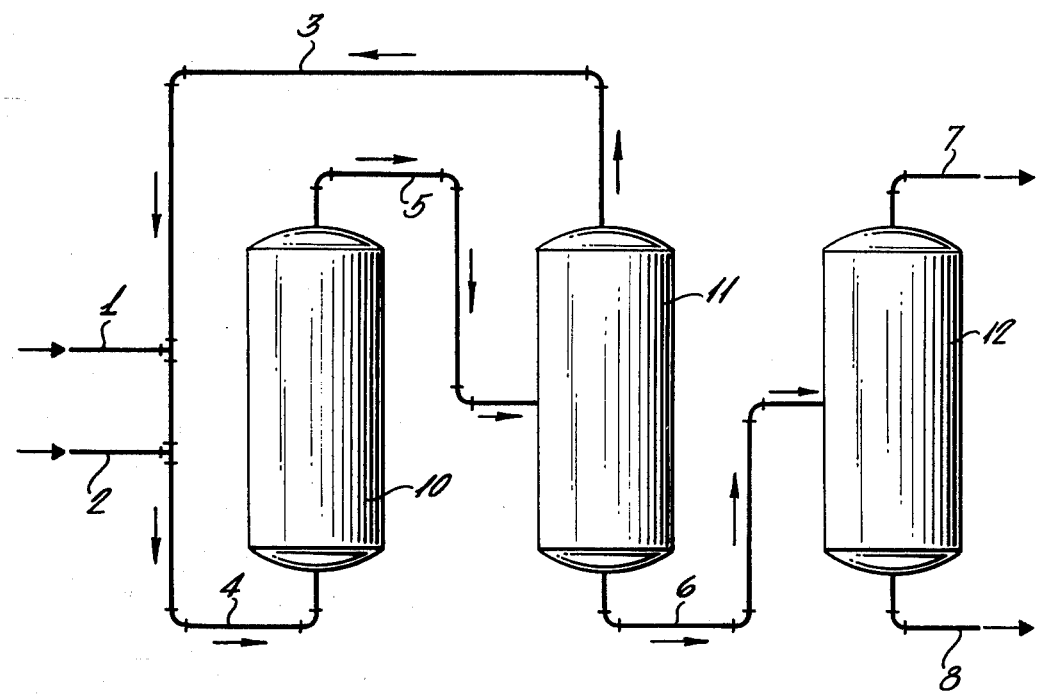

Butte, Jr. et al.

[11] 4,171,322

[45] Oct. 16, 1979

[54] HIGH SELECTIVITY CYANOETHYLATION PROCESS

[75] Inventors: Walter A. Butte, Jr., West Chester; Wesley R. Cherry, Prospect Park, both of Pa.

[73] Assignee: Suntech, Inc., Philadelphia, Pa.

[21] Appl. No.: 916,394

[22] Filed: Jun. 16, 1978

[51] Int. Cl.$^2$ .................. C07C 120/00; C07C 121/34
[52] U.S. Cl. .................................. 260/465.6; 260/464
[58] Field of Search .............................. 260/465.6, 464

[56] References Cited

U.S. PATENT DOCUMENTS

| | | | |
|---|---|---|---|
| 2,437,905 | 3/1948 | Bruson | 260/465.6 |
| 2,579,580 | 12/1951 | Howk et al. | 260/465.1 |
| 2,816,130 | 12/1957 | Selcer et al. | 260/465.6 |
| 2,836,613 | 5/1958 | Heininger | 260/465.6 |
| 2,853,510 | 9/1958 | Montagna et al. | 260/465.6 |
| 3,024,267 | 3/1962 | Howsmon, Jr. | 260/465.6 |
| 3,150,142 | 9/1964 | Eby | 260/289 |
| 3,151,150 | 9/1964 | Kamlet et al. | 260/465.6 X |
| 3,324,164 | 6/1967 | Merkel et al. | 260/465.6 X |
| 3,701,802 | 10/1972 | Maerker et al. | 260/465.6 X |
| 3,957,848 | 5/1976 | Reedy et al. | 260/465.6 |

OTHER PUBLICATIONS

Cyanoethylation; Kirk-Othmer, Encyclopedia of Chemical Technologg, 2nd ed., vol. 6, 1965, pp. 634-664.
Bruson, Org. Reactions, vol. 5, 1949, pp. 79-113.
Chem. J. Org. Chem., 27, (1962), pp. 1920-1921.

*Primary Examiner*—Joseph Paul Brust
*Attorney, Agent, or Firm*—J. Edward Hess; Donald R. Johnson; Anthony Potts, Jr.

[57] ABSTRACT

An improvement in the cyanoethylation process using a bed of basic ion exchange resin catalyst wherein the conversion of the acrylonitrile is limited to the range between from about 60% to about 96%. A monoadduct intermediate can be recycled. As a result of the limitation to the conversion selectivity as to the desired product is in excess of 95%. The improved process, e.g., has a selectivity of 98% when the conversion is about 82% and the reactants are acrylonitrile and ethylene glycol.

7 Claims, 1 Drawing Figure

HIGH SELECTIVITY CYANOETHYLATION PROCESS

CROSS REFERENCE TO RELATED APPLICATION

The subject matter of this application is related to U.S. patent application Ser. No. 916,393 filed same date by the above-identified applicants. The title of the latter application is "Continuous Cyanoethylation Process."

BACKGROUND OF THE INVENTION

This invention is directed to an improvement to a cyanoethylation process. The process involved can be continuous or batch. Cyanoethylation refers to the reaction between acrylonitrile and a variety of compounds to yield β-substituted propionitrile derivatives. The compounds are characterized by their possession of a labile hydrogen atom. The latter is a hydrogen atom bonded to an electronegative substituent. Classes of compounds containing labile hydrogen atoms include those having hydroxyl groups, e.g., polyhydric alcohols. Cyanoethylation can be generalized by the following reaction formula:

For polyhydric alcohols the general reaction formulas are as follows:

Cyanoethylation products are useful intermediates for the manufacture of plastics and fibers.

Cyanoethylation is used in the formation of a great variety of polyfunctional nitriles, for example see Encyclopedia of Chemical Technology, Kirk-Othmer, 2nd Edition, Volume 6, and Organic Reactions, R. Adams et al, Vol. 5, John Wiley and Sons, N.Y. 1949. Cyanoethylation using ion exchange resin catalyst is disclosed in J. of Org. Chem., Vol. 27, May 1962, pages 1920–1921, "Catalysis by Ion Exchange Resins. Improved Cyanoethylation and Carbamylethylation of Diols."

The cyanoethylation reaction has a tendency to be accompanied by polymerization of the acrylonitrile. It is desirable to avoid the polymerization side reaction since valuable starting material is converted to less valuable by-products. Techniques suggested to minimize the unwanted polymerization include maintaining a lower temperature by cooling the exothermic reaction, diluting the reaction mixture with an inert solvent, use of soluble or highly dispersed catalyst and the gradual addition of acrylonitrile with mechanical mixing. However, the aforementioned solutions suffered from various shortcomings such as additional capital expenditures, and/or additional materials handling costs, and/or additional separation steps and costs.

Overcoming the aforementioned problem of an unwanted side reaction and avoiding the shortcomings of the aforementioned solutions is the present invention which is an improvement to the cyanoethylation process. The improvement results in a high yield of the desired cyanoethylation product, for example 3,3'-ethylene dioxybis(propionitrile) from the reaction between ethylene glycol and acrylonitrile. In other words the amount of acrylonitrile polymer formed is minimized. Further when certain reactants are used, as disclosed hereinafter, a product intermediate can be recycled and serves as a solvent and facilitates the reaction. Still further the resulting cyanoethylated product stream is of rather high purity which simplifies subsequent processing.

SUMMARY OF THE INVENTION

In either a continuous or batch cyanoethylation process using a basic ion exchange resin catalyst bed, the improvement is that the conversion of the acrylonitrile is limited to the range between from about 60% to about 96%. The process involves removing the reaction mixture from the catalyst within the aforementioned conversion range. Then unreacted acrylonitrile and a reaction intermediate are separated from the removed reaction mixture, admixed with fresh feed comprising acrylonitrile and a polyhydric alcohol, and recycled to the reaction zone. As a result, the selectivity of the desired reaction is in excess of 95% or higher. The system, i.e., catalyst and reactants, is of a heterogeneous nature.

BRIEF DESCRIPTION OF THE DRAWING

The accompanying FIGURE is a schematic drawing of one embodiment of the improved cyanoethylation process.

EMBODIMENTS

In the FIGURE the acrylonitrile 1 and the compound containing the labile hydrogen 2 are admixed with recycle 3. The resulting mixture 4 consisting of acrylonitrile 1, a compound containing the labile hydrogen 2 and recycle 3 is introduced to reaction means 10. An inert solvent is optional. In reaction means 10 is a bed of basic ion exchange resin catalyst. Present in the reaction means 10 can be heat removal means (not shown). The reaction mixture 5 is removed from the reaction means 10 when the conversion of the acrylonitrile is between the range of from about 60% to about 96%. The reaction mixture 5 is forwarded to separation means 11, generally a distillation tower. The unreacted acrylonitrile, any reaction intermediate, which in the case of the reaction between acrylonitrile and ethylene glycol is 3-hydroxyethyleneoxypropionitrile, are separated and are recycled as recycle 3 back to reaction means 10. The bottoms 6 from separation means 11 is forwarded to separation means 12, generally a distillation tower. In separation means 12 the desired product 7 is separated from unwanted polymers and other unwanted byproducts, if any, 8. Stream 8 can be further processed or disposed of in a suitable fashion. The product 7, which is essentially the cyanoethylated product, can be processed further and converted into useful plastics and fibers. The temperature of streams 3, 5, 6, 7 and 8 can be controlled by optional heat removal means (not shown).

Reaction means 10 is designed to provide a residence time, when considering feed and recycle rates, amount of catalyst contained therein, the amount of reactant products, and inert solvent, if used, and withdrawal rates so that the desired conversion results. The residence time can range between from about a quarter of an hour to about three to five hours. Another way of indicating residence time is the amount of conversion that occurs. Conversion as used herein refers to the amount of acrylonitrile feed reacted to both desired and undesired products. The conversion by this improvement is between the range from about 60% to about 96% with a range of about 65% to about 90% preferred, while about a range of 70% to about 85% is more preferred. If a lower conversion is used then the amount of separation and recycling becomes substantial and the overall result is a less efficient process.

Because the conversion is limited to the aforementioned range recycle is generally necessary to avoid uneconomical raw material costs. The recycle will consist mostly of unreacted acrylonitrile, a monoadduct and some other materials including minor amounts of the desired diadduct. Recycling of the monoadduct permits it to react to form the desired diadduct thereby reducing raw material costs. In addition, the recycling of the monoadduct can replace the use of a solvent which helps lower costs. The amount of recycle can vary substantially. Generally, as a guide the amount of recycle can be in the range from about 10 wt. % to about 40 wt. % of the feed, i.e., polyhydric alcohol and acrylonitrile. A preferred amount of recycle is in the range from about 20 wt. % to about 30 wt. %.

As a result of limiting the conversion to the aforementioned range the selectivity is greatly enhanced. This is discussed further and data is provided under Examples. A result of the enhanced selectivity is that the amount of polymerization of acrylonitrile is substantially reduced and thus a selectivity in excess of about 95% is obtained and under more closely controlled conditions a selectively of about 98% or higher can be obtained. Because of the high selectivity, the resulting product consists essentially of a cyanoethylated product and further purification is substantially reduced, if not eliminated completely. This is another advantage of limiting conversion as disclosed herein. Selectivity, as used herein, is defined as the percent of the acrylonitrile reacted to form a useful product which includes an intermediate which can further form the desired product.

The physical form of the solid catalyst of within reaction means 10 can vary. Thus for example it can be a fixed bed or fluid bed. With such bed means several reactors can be used in series or in parallel.

The temperature of the reaction is maintained within the cyanoethylation reaction temperature range. Generally, as a guide the temperature can be in the range between from about 0° C. to about 100° C. If the temperature is too low the reaction rate will be too slow to be economical, whereas if it is too high, too much unwanted polymerization will occur and/or catalyst deactivation could be too rapid. A preferred temperature range is between from about 10° C. to about 90° C. with a range between about 30° C. to about 50° C. more preferred.

Use of an inert solvent in the cyanoethylation process is optional. If the reactants are not completely miscible a mutual solvent can advantageously serve to insure the proper stoichiometry in reaction means 10. If an inert solvent is used, the amount would be equivalent to about 20-30 weight % of the fresh feed (excluding recycle). The solvent would be a low molecular weight, non-reactive solvent, preferably boiling under about 200° C. Ethers, particularly cyclic ethers, are suitable, e.g., p-dioxane and tetrahydrofuran.

The catalyst used in this improvement is a basic ion exchange resin. The resin and variations thereof, are well-known and are described in the literature, e.g., Encyclopedia of Chemical Technology, 2nd Edition, Kirk-Othmer; Vol. 11, Ion Exchange. The amount of catalyst used in reaction means 10 depends on many variable, e.g. volume of the reaction means 10, feed rate, amount of recycle and other such variables. Life of the catalyst depends on several variables such as reaction temperature and flow rates. While any of the basic ion-exchange resins are suitable for use as a catalyst generally macroreticular types are preferred since they provide higher reaction rates.

As mentioned heretofore, one of the reactants is characterized as having a labile hydrogen atom. Examples of the polyhydric alcohols having such an atom include ethylene glycol, propylene glycol, 1,4-butylene glycol, 1,2-cyclohexanediol, etc.

The following examples illustrate the invention:

EXAMPLE

Generally the reaction of ethylene glycol and acrylonitrile was carried out in a 0.5 inch stainless steel jacketed column packed with 20 g. of basic ion exchange resin (Amberlyst A-26, Rohm & Hass). The resin was activated by washing it with 40 ml. of 10% caustic and washing with distilled water until the effluent was neutral to phenolphthalein.

A solution of 310 g. ethylene glycol and 530 g. acrylonitrile in 500 g. dioxane was charged to the top of the column and allowed to trickle through. The flow was regulated with a valve at the bottom of column. Temperature was regulated by circulation of 30° C. coolant through the jacket.

Contact time was varied over the range of 0.5 to 1.5 hr. during the course of the reaction in order to evaluate the effect of the conversion level upon selectivity. Samples of reactor effluent were analyzed by gas chromatography to determine the conversion and selectivity to ethylenedioxydipropionitrile. Samples of reactor effluent that had been contacted sufficiently to convert 95-100% of the starting acrylonitrile showed an average of 84-90% selectivity to the desired nitriles and 10-15% high boiling by-products. When conversion was limited, for example to 82% of the starting acrylonitrile, the product contained 62% dinitrile and only 1-2% high-boiling by-products. In addition, 27% mononitrile was produced that could be recycled so that the overall selectivity to nitriles was 98%, based on acrylonitrile converted, at the lower conversion level.

The accompanying Table summarizes the results of the runs made in the manner heretofore described. Listed in the Table are % conversion, % selectivity and analysis of the product and other materials.

TABLE

| EFFECT OF CONVERSION ON SELECTIVITY | | | | | | |
|---|---|---|---|---|---|---|
| Run | Conversion % | Selectivity % | Product Analysis wt. % | | | Other[b] Wt. % |
| | | | DA[a] | MA[a] | AN[a] | |
| 1 | 100 | 84 | 76.2 | 23.8 | 0 | 11.0 |
| 2 | 99.7 | 88 | 81.9 | 17.9 | 0.2 | 8.1 |
| 3 | 99.7 | 84 | 76.2 | 23.6 | 0.2 | 10.7 |
| 4 | 96.7 | 85 | 71.8 | 26.2 | 2.0 | 10.1 |
| 5 | 95.1 | 92 | 78.0 | 18.9 | 3.1 | 5.6 |
| 6 | 82.3 | 98 | 61.8 | 27.0 | 11.2 | 1.3 |

[a]DA = diadduct; MA = monoadduct; AN = acrylonitrile
[b]Other is a polymer of acrylonitrile and can contain unkowns.
[c]Selectivity equals the amount of AN in the DA plus the amount of AN in the MA, and the denominator is the aforementioned plus the other.

Comparison of data for Run 1 with Run 6 indicates that when the conversion as to the cyanoethylation of ethylene glycol decreases from 100% to 82.3% the selectivity increases from 84% to 98%. Further comparison indicates the advantage of lowering conversion, i.e., the amount of unwanted other material dropped from 11 wt. % to 1.3 wt. %.

Other polyhydric alcohols can be used in place of the ethylene glycol and similar results will be obtained. Also, other basic ion exchange resin can be used with equally similar yields.

The invention claimed is:

1. In a process for cyanoethylation of a polyhydric alcohol compound which comprises contacting said compound at cyanoethylation temperature with acrylonitrile and a cyanoethylation catalyst in a reaction zone, wherein the reaction tends to be accompanied by polymerization of acrylonitrile with resulting reduction in yield and purity of the desired cyanoethylation product, the improvement which comprises removing from the catalyst the reaction product, in which a total of 60 to 96% of the acrylonitrile required for complete cyanoethylation of said compound has been converted to cyanoethylated products and to other products, whereby the amount of products other than the desired cyanoethylation product is less than that obtained in the cyanoethylation of said compound in which the conversion of acrylonitrile exceeds 96%, and separating the desired cyanoethylation product in the reaction product from unreacted acrylonitrile.

2. Process according to claim 1, wherein said compound is an aliphatic polyhydric alcohol, and the desired cyanoethylation product is a dinitrile which is separated from unreacted acrylonitrile and from intermediate mononitrile reaction product in the reaction product mixture.

3. Process according to claim 2 wherein unreacted acrylonitrile and intermediate reaction products are recycled to the reaction zone.

4. Process according to claim 1 wherein the temperature in the reaction zone is maintained between about 0° and 100° C.

5. Process according to claim 1 wherein 65 to 90% of the acrylonitrile has been converted.

6. Process according to claim 3 wherein the cyanoethylation selectivity is in excess of 95%.

7. A continuous process for cyanoethylation of polyhydric alcohols which comprises contacting an aliphatic polyhydric alcohol with acrylonitrile and a cyanoethylation catalyst at cyanoethylation temperature in a reaction zone, removing from the reaction zone the reaction product, in which a total of 70 to 85% of the acrylonitrile required for complete cyanoethylation of said polyhydric alcohol has been converted to cyanoethylated products and to other products, separating unreacted acrylonitrile and intermediate mononitrile reaction product from the reaction product mixture, recycling said unreacted acrylonitrile and mononitrile reaction product to the reaction zone, and recovering dinitrile reaction product, whereby the amount of products other than mononitrile and dinitrile formed in the reaction zone is less than that obtained in the cyanoethylation of said polyhydric alcohol in which the conversion of acrylonitrile exceeds 85%, and whereby the selectivity of the process is in excess of 95%.

* * * * *